United States Patent [19]

Hanifl et al.

[11] Patent Number: 5,358,148
[45] Date of Patent: Oct. 25, 1994

[54] URINE COLLECTION CONTAINER

[75] Inventors: Paul H. Hanifl, Barrington Hills; Donald R. Harreld, Woodstock, both of Ill.

[73] Assignee: Sage Products, Inc., Crystal Lake, Ill.

[21] Appl. No.: 191,442

[22] Filed: Feb. 3, 1994

Related U.S. Application Data

[62] Division of Ser. No. 959,030, Oct. 9, 1992, abandoned.

[51] Int. Cl.$^5$ ............................................ B65D 37/00
[52] U.S. Cl. ..................................... 222/215; 4/144.1; 215/1 C; 222/481; 220/666
[58] Field of Search ............... 4/144.1–144.3; 215/1 C, 306; 220/375, 666, 675, 676; 222/215, 481, 482, 543, 206, 214, 215

[56] References Cited

U.S. PATENT DOCUMENTS

| | | | |
|---|---|---|---|
| 2,758,755 | 8/1956 | Schafler | 222/215 X |
| 2,857,080 | 10/1958 | Elias | 222/215 X |
| 3,156,383 | 11/1964 | Melli | 222/215 X |
| 3,182,861 | 5/1965 | Nataf | 215/1 C X |
| 3,227,332 | 1/1966 | Gowdy et al. | 222/543 X |
| 3,456,850 | 7/1969 | Uhlmann | 222/482 X |
| 4,270,231 | 6/1981 | Zint | 4/144.1 |
| 4,317,525 | 3/1982 | Schuessler et al. | 215/1 C |
| 4,836,416 | 6/1989 | Shalgi et al. | 222/543 X |

*Primary Examiner*—Charles E. Phillips
*Attorney, Agent, or Firm*—Lee, Mann, Smith, McWilliams, Sweeney & Ohlson

[57] ABSTRACT

A sealed collection container having a hollow container body formed of semi-rigid material, such as plastic. The container body is provided with a sealable opening, and a non-venting spout which permits liquid to be poured from the container when inverted. The spout, in combination with deformable sides of the container form a system for metering a desired quantity of liquid from the container when inverted. The deformable sides can be formed thinner in thickness than the corner portions of the container from which the sides extend to aid the metering function of the container.

15 Claims, 1 Drawing Sheet

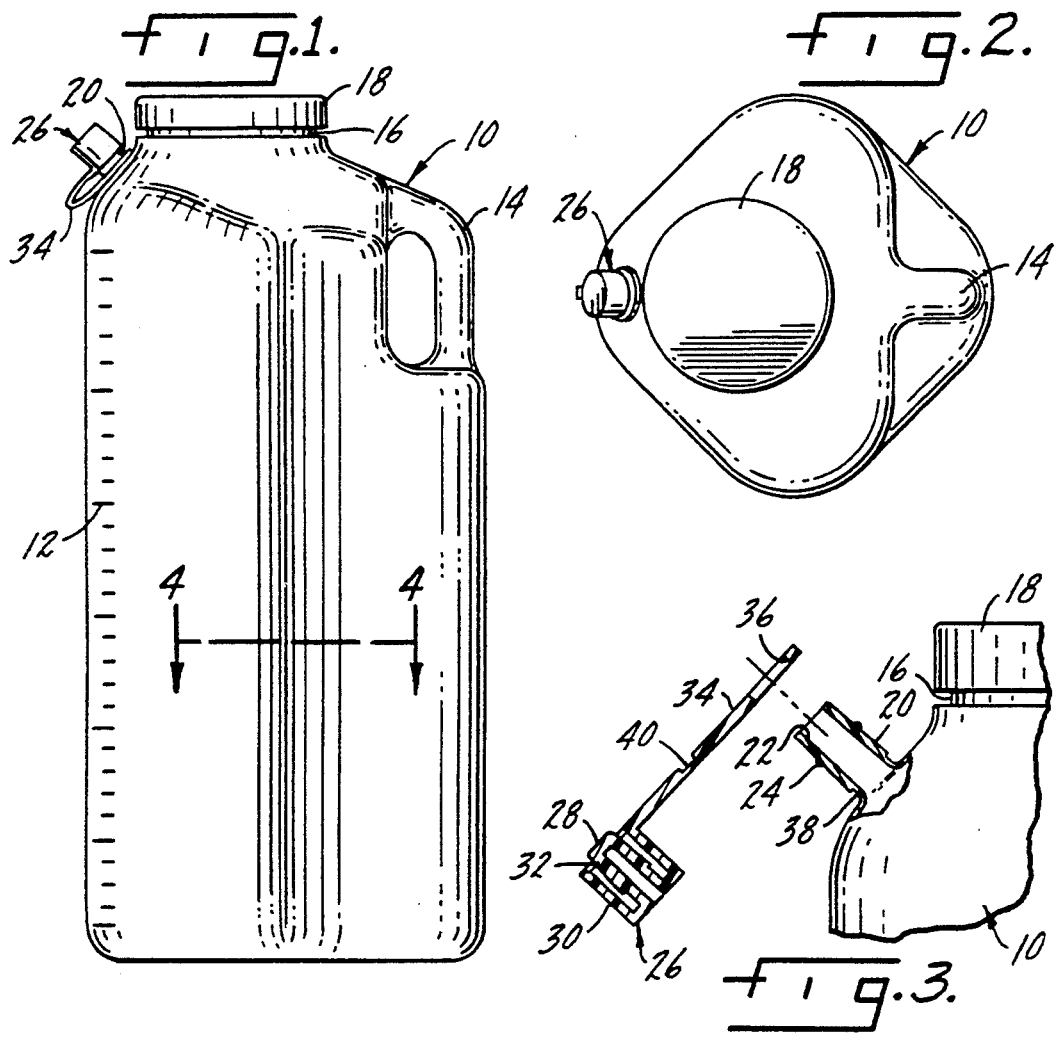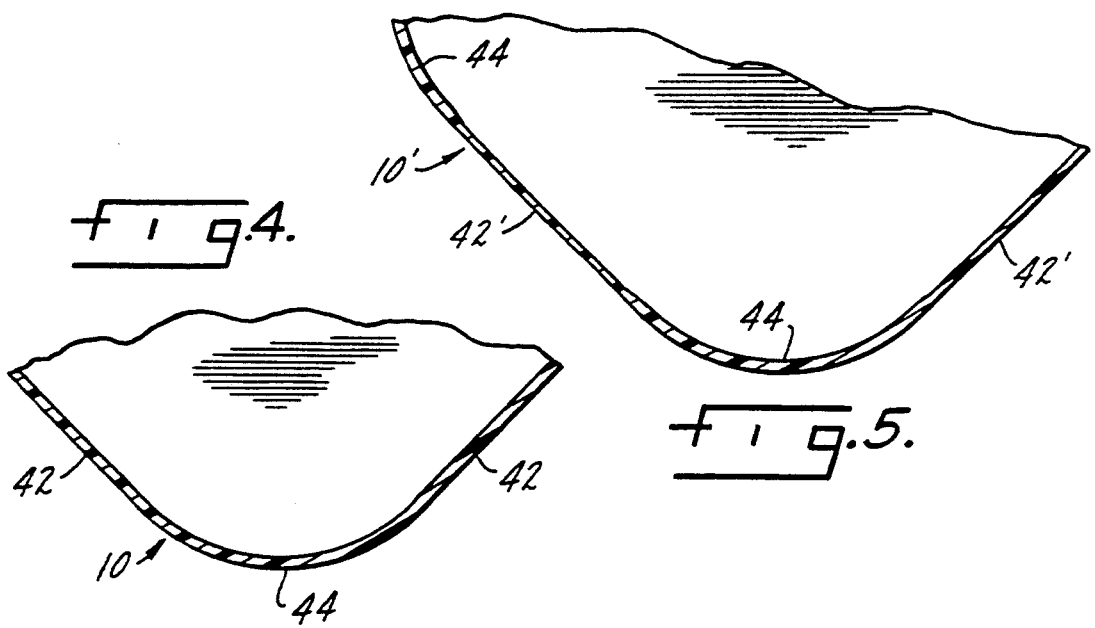

URINE COLLECTION CONTAINER

This application is a division, of application Ser. No. 07/959,030, filed Oct. 9, 1992 now abandoned.

BACKGROUND OF THE INVENTION

This invention relates to containers, and in particular to a sealed collection container preferably for collection of urine and which includes means for metering from the container a desired quantity of urine when the container is inverted.

The container of the invention is typically employed for collection of urine, body fluids or other liquids over a determined period of time. After collection, the liquid is then typically tested by various means or otherwise processed.

Since the container is large and collection can be over a long period of time, it is important that liquid withdrawn from the container be withdrawn safely and, preferably, in a measured quantity. In the past, such containers have been formed of plastic with a large opening at the top, and quantities of liquid are simply withdrawn by removing the cap for the opening, and pouring out a desired volume of liquid. However, such a process is susceptible to spilling, contamination, and it is difficult to accurately meter desired quantities of liquid without using other apparatus to withdraw the liquid.

SUMMARY OF THE INVENTION

The invention improves upon previous collection containers by providing a sealed collection container comprising a hollow container body formed of semi-rigid material, the container body having a top and a bottom and a plurality of deformable sides. An opening is provided in the top of the container body and means is provided for closing and sealing the opening. A non-venting spout is provided in the top of the container body adjacent to the opening, the spout being of a size to permit liquid to be poured from the container when inverted without permitting venting air to enter the spout. The container includes means for metering a desired quantity of liquid exiting the container when inverted, the metering means comprising the spout in combination with the deformable sides of the hollow container body. Finally, means is provided for capping the spout.

In accordance with the preferred form of the invention, the spout includes an upstanding nozzle, and the capping means comprises a stopper for the nozzle. The stopper includes a plug portion engageable within the nozzle and an annular cap spaced from the plug, the cap and the plug being spaced sufficiently to grip the nozzle therebetween when the stopper is installed on the nozzle. The container and its parts are preferably formed of plastic, and the nozzle includes at least one exterior annular collar shaped to engage the cap to enhance the grip of the nozzle when the stopper is installed on the nozzle. Preferably, the plug portion of the stopper also includes a tapered wall extending from a distal end of the plug portion to enhance the frictional engagement of the plug portion and the nozzle.

In accordance with the preferred form of the invention, the stopper includes an extended, flexible tether secured to the container body. The tether includes a securing ring at a distal end of the tether, the ring being shaped to engage about the nozzle. The nozzle includes an annular groove, with the ring engaging the groove to be held in place.

In the preferred form of the invention, the thickness of the wall of the container is generally the same throughout, and the plastic of the container and the thickness of the walls are such that the walls are deformable. In accordance with another form of the invention, the deformable sides can be thinner in thickness than the corner portions of the container from which the sides extend so that the sides may deform or be squeezed. In either form of the invention, the spout is non-venting when the container is inverted so that venting air will not normally enter the container.

BRIEF DESCRIPTION OF THE DRAWINGS

The invention is described in greater detail in the following description of an example embodying the best mode of the invention, taken in conjunction with the drawing figures, in which:

FIG. 1 is an elevational view of a collection container according to the invention, FIG. 2 is a top plan view thereof, FIG. 3 is an enlarged elevational view of a portion of the top of the collection container, part of which is in cross section, illustrating detail and showing the manner in which the stopper attaches to the container, FIG. 4 is an enlarged cross sectional view taken along lines 4—4 of FIG. 1, and FIG. 5 is a cross sectional view similar to that of FIG. 4, but showing a bit more of the collection container and illustrating a second form of the invention in which the sides of the container are thinner in thickness than the corner portions of the container.

DESCRIPTION OF EXAMPLES EMBODYING THE BEST OF THE INVENTION

A sealed collection container according to the invention is shown generally at 10 in the drawing figures. The container 10 is hollow, and preferably is blow molded from plastic in a conventional fashion. The container 10 includes gradations 12 and an integral handle 14 which is used for transportation of the container 10. Since the container 10 is preferably a large container (on the order of three liters) for long term collection of fluids, the handle 14 is a useful part, but it may be omitted if desired.

The container 10 includes a large opening 16 at the top thereof, and a closure 18 applied thereto in a conventional fashion, such as on screw threads (not illustrated), so that the closure 18 can be removed and reapplied, and, when applied, seals the opening 16. The closure 18 forms no part of the invention other than providing a closure and a seal for the opening 16 in the top of the container 10. Containers with such an opening and a closure (but without the remaining aspects of the invention) are well-known, and the closure 18 typically is removed during the time that fluids are collected in the container 10.

The container 10 also includes a non-venting spout in the top of the container adjacent to the opening 16. The spout is in the form of an upstanding nozzle 20, preferably formed as an integral portion of the container 10 during the molding thereof.

The nozzle 20 is annular, having an essentially cylindrical, smooth inner wall 22. The exterior of the nozzle 20 is also cylindrical, and preferably includes at least one exterior annular collar 24 as shown in FIG. 3.

A stopper 26 is provided for capping and sealing the nozzle 20. The stopper 26 comprises a plug portion 28 shaped to be frictionally engaged with the wall 22 within the nozzle 20, and an annular cap 30 which is spaced from the plug portion 28. As best shown in FIG. 3, the plug portion 28 and the cap 30 are spaced sufficiently to grip the nozzle 20 therebetween when the stopper 26 is installed on the nozzle. When thus installed, the collar 24 engages the cap 30 to enhance the grip of the nozzle by the stopper 26.

The plug portion 28 includes a tapered wall 32 extending from a distal end of the plug portion to enhance the frictional engagement of the plug portion 28 and the inner wall 22 of the nozzle 20. The wall 32 tapers outwardly so that the farther stopper 26 is installed on the nozzle 20, the tighter the frictional engagement between the stopper 26 and the nozzle 20.

To retain the stopper 26 on the container 10, the stopper 26 includes an extended, flexible tether 34. The tether 34, which may be an integral extension from the stopper 26, includes a securing ring 36, the ring 36 being shaped to be engaged over the nozzle 20. The nozzle 20 also includes an annular groove 38 at the base of the nozzle 20 and the ring 36, when fitted over the nozzle 20, is seated in the annular groove 38. The stopper 26 and extended tether 34 are preferably formed of plastic, and therefore the ring 36 is formed slightly smaller than the outer diameter of the nozzle 26 so that the ring 36 is stretched when installed over the nozzle 20 until it is seated in the annular groove 38.

The tether 34 folds upon itself when the stopper 26 is in the closed position, as shown in FIG. 1. To facilitate folding of the tether 34, the tether includes a notch 40 at the natural hinge location of the tether 34 when folded.

The nozzle 20 is non-venting when the container 10 is inverted. That is, the nozzle 20 has a small enough inner dimension so that when the container 10 is inverted, although liquid may be expelled from the container due to partial collapsing of the sides of the container, air will not enter through the nozzle 20. As explained above, preferably the container is formed of plastic which has flexibility, and as shown in FIG. 4, the container 10 has sides 42 extending from corners 44 thereof which are essentially of the same wall thickness. When the container 10 is inverted, the sides 42 can be squeezed to expel liquid therefrom, or the sides 42 can be permitted to naturally deform slightly to meter a desired quantity of liquid from the container 10. After the walls have deformed, however, because the nozzle 20 is non-venting, no additional liquid can be expelled from the container 10. Therefore, the container 10 is self-metering due to the nature of the deformable sides 42 and the non-venting nature of the nozzle 20.

In some instances, the walls 42 may be too thick to readily deform, or the plastic material of the container 10 may be such that relatively thick walls 42 do not easily deform. To promote deformation of the walls in this instance, and as shown in FIG. 5, the sides 42' between the corners 44 may be made relatively thinner so that the sides are flexible, but the corners are essentially rigid. When the container 10' of FIG. 5 is inverted, the thinner sides 42' deform and, in combination with the non-venting spout formed by the nozzle 20, permit metering of a desired quantity of liquid from the container 10'. Thus, by judicious selection of the plastic material of the container 10 or 10', in combination with the thickness of the walls thereof, the container 10 or 10' can be formed to meter desired quantities of liquid therefrom by simple inversion of the container 10 when the stopper 26 has been opened. Additional liquid can be poured from the container by either squeezing the walls of the container, or by returning the container to the upright orientation (thus permitting venting through the nozzle 20) and then re-inverting the container to again meter the desired quantity of liquid from the container. Of course, the closure 18 can always be removed to pour any desired quantity of liquid from the container 10.

The container 10 has been developed for long term collection of urine, where testing is periodically conducted. Since desired quantities of urine must be tested, the container 10 can be formed so that, when it is inverted, such a desired quantity, but only that desired quantity, is expelled when the container is inverted. The remaining liquid within the container remains in the container unless the container is squeezed or is re-inverted.

Various changes can be made to the invention without departing from the spirit thereof or scope of the following claims.

What is claimed is:

1. A sealed collection container comprising
  a. a hollow container body formed of semi-rigid material, said container body having a top and a bottom and a plurality of deformable sides, each side extending between relatively non-deformable corner portions of said container body;
  b. an opening in the top of said body,
  c. means closing and sealing said opening,
  d. a non-venting spout in the top adjacent said opening, said spout being of a size to permit liquid to be poured from the container when inverted without permitting venting air to enter the spout,
  e. means for metering a desired quantity of liquid exiting said container when inverted, comprising said spout in combination with said deformable sides, such that upon inverting said container with fluid therein and the spout open, the sides of said container will naturally slightly deform to meter a quantity of liquid from said container and
  f. means capping said spout.

2. A sealed collection container according to claim 1 in which said spout includes an upstanding nozzle, and said capping means comprises a stopper for said nozzle.

3. A sealed collection container according to claim 2 in which said stopper includes a plug portion frictionally engageable within said nozzle and an annular cap spaced from said plug portion, said plug portion and said cap being spaced to grip the nozzle therebetween when said stopper is installed on said nozzle.

4. A sealed collection container according to claim 3 in which said nozzle includes at least one exterior annular collar shaped to engage said cap to enhance the grip of said nozzle.

5. A sealed collection container according to claim 3 in which said plug portion includes a tapered wall extending from a distal end of said plug portion to enhance the frictional engagement of said plug portion and said nozzle.

6. A sealed collection container according to claim 2 in which said stopper includes an extended, flexible tether secured to said container body.

7. A sealed collection container according to claim 6 in which said tether includes a securing ring at a distal end, said ring being shaped to engage about said nozzle.

8. A sealed collection container according to claim 7 in which said nozzle includes an annular groove, said ring engaging said groove.

9. A sealed collection container according to claim 1 in which said deformable sides are thinner in thickness than corner portions of said container from which said sides extend.

10. A sealed collection container with liquid metering, comprising,
   a. a hollow container body formed of semi-rigid material, said container body having a top and a bottom and a plurality of deformable sides, each side extending between relatively non-deformable corner portions of said container body,
   b. an opening in the top of said body,
   c. means closing and sealing said opening,
   d. a non-venting spout in the top adjacent said opening, said spout being of a size to permit liquid to be poured from the container when inverted without permitting venting air to enter the spout, said spout including an upstanding hollow nozzle,
   e. said deformable sides being thinner in thickness than the corner portions of said container from which said sides extend,
   f. means for metering a desired quantity of liquid exiting said container when inverted, comprising said spout in combination with said deformable sides, such that upon inverting said container with fluid therein and the spout open, the sides of said container will naturally slightly deform to meter a quantity of liquid from said container and
   g. a stopper for capping said spout, said stopper including a plug portion engageable within said nozzle and an annular cap spaced from said plug, said plug and said cap being spaced to grip the nozzle therebetween when said stopper is installed on said nozzle.

11. A sealed collection container according to claim 10 in which said nozzle includes at least one exterior annular collar shaped to engage said cap to enhance the grip of said nozzle.

12. A sealed collection container according to claim 10 in which said plug portion includes a tapered wall extending from a distal end of said plug portion to enhance the frictional engagement of said plug portion and said nozzle.

13. A sealed collection container according to claim 10 in which said stopper includes an extended, flexible tether secured to said container body.

14. A sealed collection container according to claim 13 in which said tether includes a securing ring at a distal end, said ring being shaped to engage about said nozzle.

15. A sealed collection container according to claim 14 in which said nozzle includes an annular groove, said ring engaging said groove.

* * * * *